United States Patent [19]

Cone et al.

[11] Patent Number: 5,108,377
[45] Date of Patent: * Apr. 28, 1992

[54] MICRO-INJECTION PORT

[75] Inventors: Lori L. Cone; Arthur L. Rosenthal, both of Cranston, R.I.; Michael A. Nadeau, No. Attleboro, Mass.

[73] Assignee: C.R. Bard, Inc., Murray Hill, N.J.

[*] Notice: The portion of the term of this patent subsequent to Apr. 10, 2007 has been disclaimed.

[21] Appl. No.: 507,035

[22] Filed: Apr. 9, 1990

Related U.S. Application Data

[63] Continuation of Ser. No. 151,406, Feb. 2, 1988, Pat. No. 4,915,690.

[51] Int. Cl.⁵ ............................................. A61M 5/32
[52] U.S. Cl. ................................... 604/175; 604/93
[58] Field of Search ........................... 604/93, 86, 8-10, 604/175, 891.1, 24

[56] References Cited

U.S. PATENT DOCUMENTS

| | | | |
|---|---|---|---|
| 4,181,132 | 1/1980 | Parks | 128/899 |
| 4,496,343 | 1/1985 | Prosl et al. | 604/86 |
| 4,543,088 | 9/1985 | Bootman et al. | 604/93 |
| 4,569,675 | 2/1986 | Prosl et al. | 604/175 |
| 4,710,167 | 12/1987 | Lazorthes | 604/93 |
| 4,710,174 | 12/1987 | Modew et al. | 604/244 |
| 4,781,695 | 11/1988 | Dalton | 604/93 |
| 4,846,806 | 7/1989 | Wigness et al. | 604/175 |
| 4,886,501 | 12/1989 | Johnston et al. | 604/175 |
| 4,904,241 | 2/1990 | Bark | 604/93 |
| 4,915,690 | 4/1990 | Cone et al. | 604/93 |

Primary Examiner—Stephen C. Pellegrino
Assistant Examiner—Ralph A. Lewis
Attorney, Agent, or Firm—Wolf, Greenfield & Sacks

[57] ABSTRACT

A micro-injection port having a low profile is provided. The micro-injection port has a septum and an injection chamber located side-by-side. When implanted, the puncture surface of the septum lines substantially perpendicular to the surface of the the micro-injection port also has a filter systems skin. The filter is formed from an opening in the side wall of the injection port and a shaft secured within the opening.

10 Claims, 5 Drawing Sheets

MICRO-INJECTION PORT

This application is a continuation of application Ser. No. 151,406, filed Feb. 2, 1988, now U.S. Pat. No. 4,915,690.

BACKGROUND OF THE INVENTION

This invention relates to subcutaneously implanted injection ports, filter systems for such ports and methods of implanting such ports.

A subcutaneous injection port is a totally implantable device designed to provide repeated access to a body space such as the vascular system. Injection ports typically include an injection chamber accessible through a septum, the injection chamber being connected by an exit port and catheter to the desired body space. The device is implanted just beneath the skin, and the injection chamber may be accessed repeatedly by passing a needle through the skin and septum.

Currently marketed subcutaneous injection ports typically are top-entry devices. In a top entry device, the septum is stacked on top of the injection chamber, and the puncture surface of the septum is located parallel to the skin when implanted. The injection chamber is accessed by passing a needle through the skin perpendicular to the septum and skin. Such perpendicular access requires a relatively tall device because the injection chamber must be deep enough to accept the needle opening and the septum must be thick enough to insure a leakproof seal after repeated punctures. While such relatively tall top-entry devices are useful in certain instances in adults, they can only be scaled down a certain amount and are not so useful in pediatric patients or in particular locations in other patients where a tall device may result in tissue damage.

Another drawback of top-entry devices is that specially designed right-angle needles are usually used when long-term infusion is contemplated. The distal end of the right angle needle is inserted through the skin and septum and into the injection chamber of the top-entry device, with the proximal end of the needle lying parallel to the skin. This proximal end then is taped to the skin to secure the needle in place. These right-angle needles are known to back out of the chamber due to movements by the patient. Further, the length of the distal end of the right-angle needle must be closely matched to the depth of the implanted port. This sometimes requires trial and error of different sized needles with repeated puncture of the skin. Such repeated puncture is undesirable.

Another drawback of the top entry device is that when semi-rigid catheters are used for long-term access, special anti-kink brackets are required to allow the catheter which exits perpendicularly to the skin to be bent over and taped to the skin without kinking.

Another drawback of typical top-entry devices is that expensive non-coring needles, such as a Huber-type needle, must be used when accessing the injection chamber via the septum. The septums of such devices are relatively wide and have a short puncture length relative to the width. To allow repeated puncture, the septum must be captured under substantial compression. The compression is of a degree that a standard needle would core the septum.

Further, implanted ports sometimes flip over. Flipping is particularly likely with small devices. The overturning of the prior art top-entry devices renders their septum inaccessible.

It is desirable to use a filter in a subcutaneous injection port to prevent particles introduced into the port's chamber from entering into the body space accessed by the chamber. For example, particles of fat, skin, dust, rubber and plastic sometimes are introduced into the injection chamber of the implanted port as a needle is passed into and through the skin and septum to access the chamber. The danger to the patient from such particles is of increased concern in pediatric patients whose relatively smaller body passages may become blocked more easily than the larger passages of adults. Therefore, a pediatric injection port not only should have a low profile, but also should have a filter. However, manufacturing a filter for an injection port as small as the device of the present invention is problematic.

SUMMARY OF THE INVENTION

The micro-injection port of the invention has a septum and injection chamber located side by side, rather than stacked on top of one another. When implanted, the puncture surface of the septum lies substantially perpendicular to the surface of the skin, rather than parallel to the surface of the skin as in the top-entry devices. This side-by-side arrangement substantially reduces the height of the device making the device useful in small children or infants, or in places in adult patients where the skin is not protected by fatty tissue. The reduced height or low profile of the side-entry injection port also renders the device more desirable from a cosmetic point of view when implanted.

While the foremost advantage of the side-entry injection port is its decreased height, the device has many other advantages. Because the puncture surface of the septum is located on the side of the device and oriented substantially perpendicular to the surface of the skin, if the device flips over, the septum still is accessible. Likewise, this side placement of the septum allows for long-term access of the injection chamber using a straight needle. According to the invention, a needle is passed substantially parallel to the surface of the skin, through the skin and septum and into the injection chamber. The portion of the straight needle outside the skin lies substantially parallel against the surface of the skin. It, therefore, is easy to secure the needle in place flat against the skin simply by taping it. Relative motion between the skin surface and muscle fascia does not result in accidental needle withdrawal because the relative motion is perpendicular to the plane of injection. Moreover, a right-angle needle is not required and, therefore, it is not necessary to closely match the length of the needle to the depth of the implanted port. Further, a standard needle, rather than a special non-coring needle may be used because the puncture length of the septum is relatively long and the septum is captured under relatively low compression.

The side entry injection port has a rigid housing with rigid walls defining an injection chamber. The housing may have a substantially flat top wall, a substantially flat bottom wall and a side wall connecting the periphery of the top and bottom walls. Preferably the housing is in the shape of a disk, with the top and bottom walls being concentric and the bottom wall being slightly larger than the top wall to stabilize the device against flipping. The side wall has an opening and a septum is captured by the housing to seal the opening. The exposed puncture area of the septum occupies a substantial portion of the projected sidewall area of the housing when viewed along the centerline of the septum. An exit port located opposite the septum communicates with the injection chamber through the side wall.

The side-entry injection port has a filter system to prevent particles introduced into the injection chamber from entering the body. The filter is formed from an opening in the side wall of the housing and a shaft secured within the opening. A first portion of the shaft is sized to sealingly mate with the opening and the second portion of the shaft has a cross-sectional area less than the cross sectional area of the opening at or close to the inside surface of the side wall. The second portion of the shaft and the opening define a space. The smallest cross-sectional area of this space defines the filter. The space communicates with an exit bore through the shaft such that fluid introduced into the injection chamber may exit the injection chamber by passing into the space and out the exit bore.

Preferably the shaft has a barbed portion extending from the side wall of the injection port for a catheter attachment site. Thus, the shaft and the opening in the side wall of the housing together act as a filter, an exit port and a catheter attachment site. Preferably, a suture tab is secured to the barbed portion of the shaft. The suture tab is sutured to the tissue when the device is implanted and the device may be rotated somewhat about the axis defined by the suture point.

It is an object of the invention to provide a device having the foregoing features and it is a further object of the invention to provide such a device that is easy to manufacture and has few parts.

DETAILED DESCRIPTION OF THE DRAWINGS

Figure 1A:
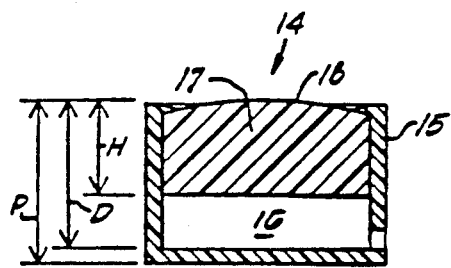
FIG. 1A is a schematic cross-sectional representation of the injection port of the prior art.
Figure 1B:
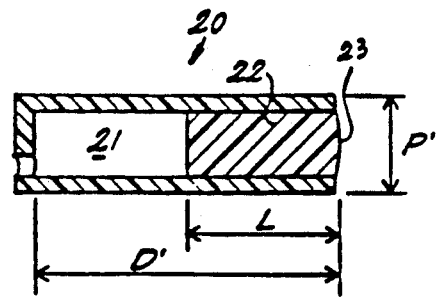
FIG. 1B is a schematic cross-sectional representation of the injection port of the invention.

The injection port of the invention is schematically shown in cross-section and compared to the prior art in FIG. 1. The typical prior art device is a top-entry injection port 14 having a rigid housing 15 defining an injection chamber 16 accessible through septum 17. In a top-entry injection port 14, the septum 17 is stacked on top of the injection chamber 16. When implanted, the puncture surface 18 of the septum is located substantially parallel to the surface of the skin and the height or profile P of the device is defined at a minimum by the height of the injection chamber 16 plus the height of the septum 17.

The side-entry injection port 20 of the invention places the injection chamber 21 and the septum 22 side-by-side, rather than stacked on top of one another. When implanted, the puncture surface 23 of the septum 22 is located substantially perpendicular to the surface of the skin, and the profile P' of the device is defined by the height of the septum, not the height of the septum added to the height of the injection chamber. Because the profile is substantially reduced as compared to the prior art top-entry devices, the invention is useful in environments in which top-entry devices are not useful.

The invention's side-entry arrangement also allows for increasing the useful life of the septum without increasing the height of the septum and, correspondingly, the height of the device. The useful life of the septum may be increased by increasing the puncture length of the septum. The puncture length of the septum may be defined by the distance of the septum through which a needle must travel to access the injection chamber. Generally, the longer this distance, the greater the number of punctures the septum can withstand without leaking.

In a top entry device, the puncture length corresponds to the height H of the septum 17. If this puncture length or height H is increased, then so is the overall profile P of the device. In the side-entry injection port of the invention, the puncture length corresponds to the length L of the septum 22, the length running parallel to the surface of the skin. If this puncture length L is increased, then only the overall length of the device is increased. The height or profile P' of the device remains the same.

The side-entry injection port of the invention may be distinguished from the prior art in another respect. In the top-entry injection port of the prior art, the distance D from the puncture surface 18 of the septum to the wall of the injection chamber opposite the septum 17 is always less than the profile P of the device. In the side entry port of the invention, the distance D' from the puncture surface 23 of the septum 22 to the wall of the injection chamber opposite the septum 22 may be much greater than the profile P' of the device. In fact, the puncture length L of the septum 22 alone may be greater than the profile P' of the device.

Figure 2:
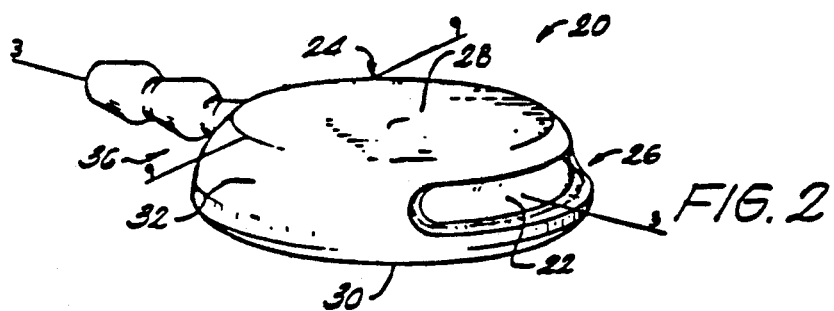
FIG. 2 is a side elevated view of the preferred embodiment of the invention.
Figure 3:
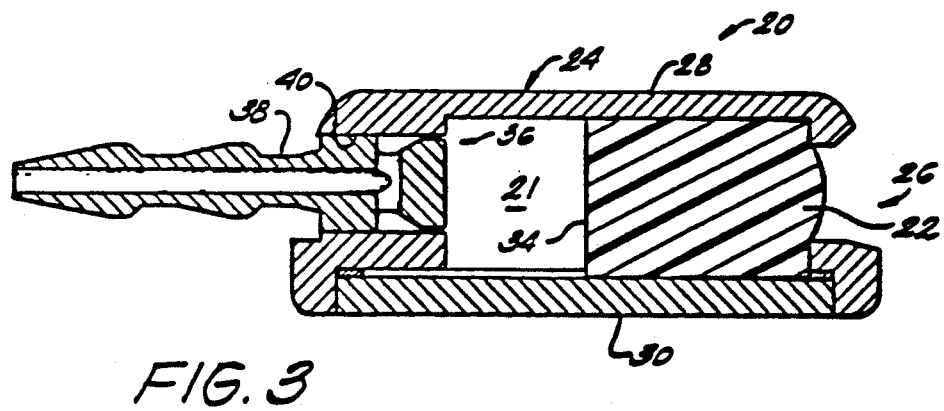
FIG. 3 is a cross-sectional view along lines 3—3 of FIG. 2.

Referring to FIGS. 2 and 3, the preferred embodiment of the invention is a side-entry injection port 20 having a housing 24 shaped substantially like a disk. The housing 24 is made of a rigid material, such as metal, and defines an internal injection chamber 21 accessible through an opening 26 in the housing 24, which opening 26 is sealed by the septum 22. A biocompatible metal is preferred over plastic because a metal housing generally requires thinner walls to achieve the desired rigidity and compression on the septum. An implant grade Titanium alloy has been used successfully.

The housing 24 preferably has flat, parallel disk shaped top and bottom walls, 28 and 30, respectively, which walls are connected along their periphery by a side wall 32. The top and bottom walls 28, 30 are concentric with the top wall 28 somewhat smaller than the bottom wall 30. The side wall 32 slopes gently from the periphery of the top wall 28 to the periphery of the bottom wall 30. Preferably, the device has rounded corners to minimize tissue irritation when implanted. The top, bottom and side walls 28, 30, 32 along with chamber-facing surface 34 of the septum 22 together define the injection chamber 21.

The opening 26 is in the side wall 32 of the housing 24 and is sealed off by the septum 22. The opening 26 extends approximately 80° around the circular side wall 32. The remainder of the side wall 32 is solid, except for an exit port 36, which exit port provides an exit path for fluid introduced into the injection chamber 21.

The exit port 36 communicates with the injection chamber 21 and is located in the side wall 32 opposite the septum 22. The exit port 36 in the preferred embodiment is defined by a port outlet connector 38 fitted into a bore 40 in the side wall 32 of the housing 24. The port outlet connector 38 and the bore 40 in the side wall 32 together serve as a filter system, an exit port and a catheter attachment site for the side-entry injection port 20 of the invention. These features are discussed in greater detail below.

Figure 4:
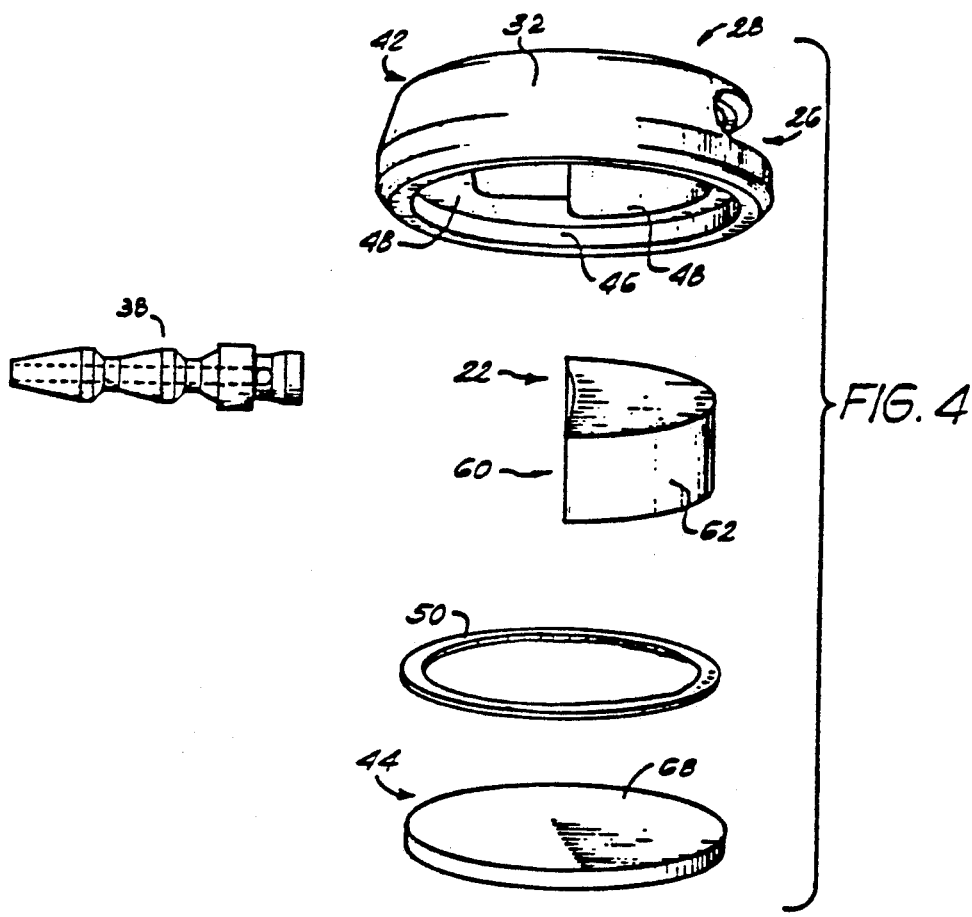
FIG. 4 is an exploded view of FIG. 2.

The low profile injection port 20 is shown in an exploded view in FIG. 4. The rigid housing 24 is constructed from two separate elements, a top element 42 and a bottom element 44. The top element 42 defines the top wall 28 and the side wall 32 of the injection port 20. A lip 46 extends about the periphery of the side wall 32 to form a seat or step 48 also extending completely about the periphery of the side wall 32. The step 48 is parallel to the top wall 28 and is provided to mate in face-to face relation with the bottom element 44 when the device is assembled. The bottom element 44 is sized to fit just within the lip 46.

The top and bottom elements 42, 44 capture a gasket 50 and the septum 22. The gasket 50 is sized to fit within the lip 46 and between the facing surfaces of the bottom element 44 and the step 48. The gasket 50 is essentially a silicone rubber ring and is captured between the top and bottom elements to form a leak-proof seal.

Figure 5:
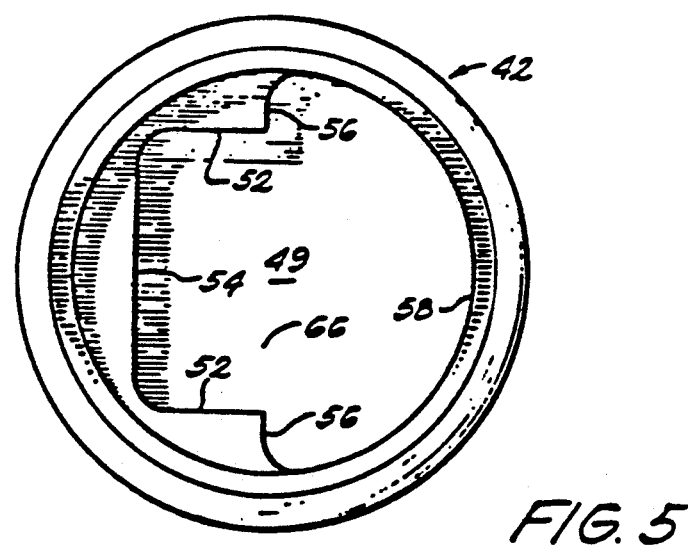
FIG. 5 is a bottom view of the top element of FIG. 4.

The top element 42 has a hollowed out center 49. Referring to FIG. 5, the hollowed out center has the profile of a doorknob. There is a neck region and a head region. The neck region has neck side walls 52 connected at one end by a neck base wall 54. The head region defines a shape similar to a slice of a disk. The head region has two shoulder walls 56, one each extending perpendicularly from each of the neck side walls 52, and has an arcuate front wall 58 connecting the free ends of the shoulder walls 56.

The septum 22 is sized to fit compressively within the head region. Referring to FIG. 4, the septum also is shaped similar to a slice of a disk, having a chamber-facing wall 60 and an arcuate septum front wall 62. The septum front wall 62 mates with the arcuate front wall 58 of the head region and the ends of the chamber-facing wall 60 mate with the shoulder walls 56 of the head region.

Figure 6:
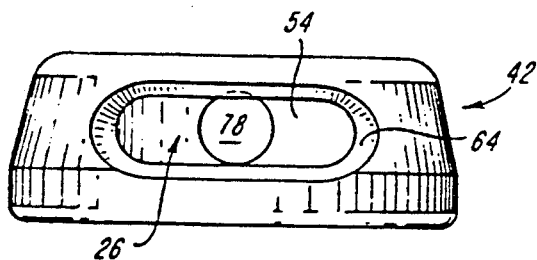
FIG. 6 is a front view of the top element of FIG. 4.

The opening 26 in the top element 42 is shown in detail in FIG. 6. The opening 26 has a beveled edge 64. It is centered relative to the arcuate front wall 58 and is located directly across from the neck base wall 54. The exit port 36 is located and centered in the neck base wall 54.

When assembled, the top and bottom elements 42, 44 compressively capture the gasket 50 and the septum 22. The bottom element 44 is provided with a chamfer (not shown) so that it may be interference-fit together with the top element 42. The neck side and neck base walls 52, 54 together with the chamber-facing surface 34 of the septum 22 define the side walls of the injection chamber 21. The inside surface 66 of the top wall 28 and the inside-facing surface 68 of the bottom element 44 form the top and bottom walls of the injection chamber 21.

The seal formed by the septum 22 against the opening 26 and the seal formed by the gasket 5 between the top and bottom elements 42, 44 preferably is sufficient to withstand 45 p.s.i. air pressure without leaking for 5 seconds. The device preferably will withstand this pressure even after 500 needle punctures using a 23 gage hypodermic or 20 gage non-coring needle. Thus, if the delivery catheter connected to the injection port when implanted becomes occluded, then fluid may be introduced into the injection chamber without leaking of the fluid. A successful embodiment has been made using a septum made of silicone rubber, having a durometer of 50 and a puncture length of 0.240". The septum is compressed to a degree whereby the height of the septum is reduced by about 12.5%.

When used in pediatric patients, the side entry injection-port 20 has a height of about ⅜" (0.375") or less. In the embodiment described, the height is about 0.225". Preferably the volume of the injection chamber is not less than 5 microliters.

The size of the opening 26 is important. Preferably the opening 26 extends less than 180° about the periphery of the side wall 32, with the remainder of the side wall 32 being solid (except for the exit port). The solid portion of the side wall then will act as a stop for a needle inserted into the injection chamber. When the needle is inserted through the septum it will contact the inside surface of the rigid side walls of the housing and will not come out the other side of the device. Further, if the opening extends too far about the periphery of the side walls it is also difficult to capture the septum and gasket under enough compression to achieve a device that will withstand the 45 PSI air pressure without leaking for five seconds. These problems are obviated somewhat as the size of the device and, correspondingly, the size of the injection chamber and the thickness of the rigid walls are increased. In the embodiment described, the opening is 0.34" across its face and 0.1" high.

It is also important that the opening be large enough so that the puncture surface of the septum, which is defined by the opening, may be located when the device is implanted. The puncture surface of the septum, therefore, should occupy a substantial portion of the projected side wall area of the housing when viewed along the centerline of the septum, as shown in FIG. 6.

Figure 7:
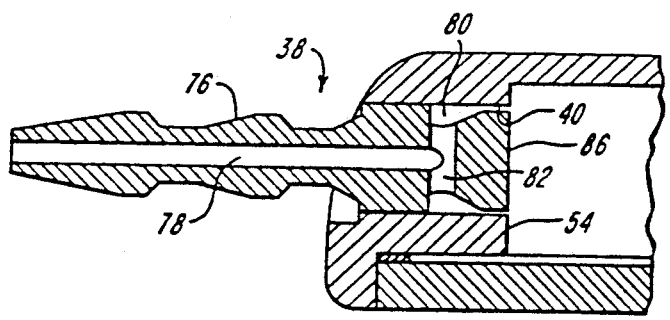
FIG. 7 is an enlarged view of the exit port region of FIG. 3.
Figure 8:
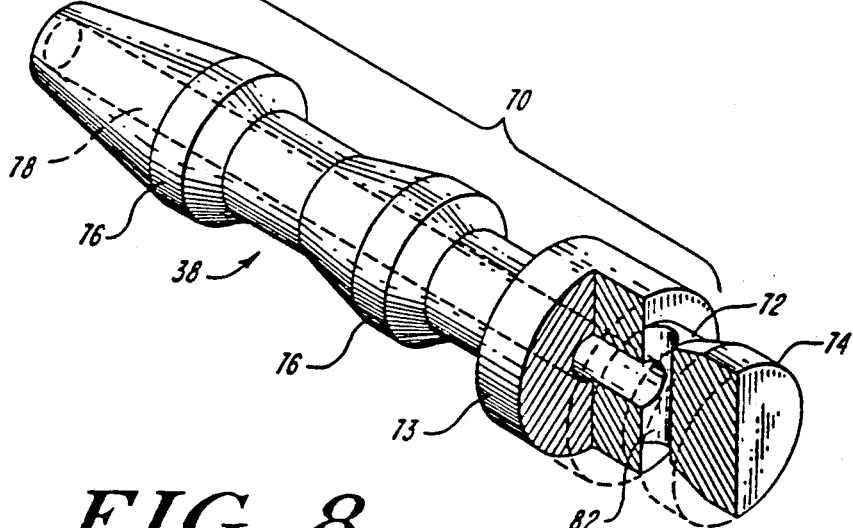
FIG. 8 is an enlarged cross-sectional view of the port outlet connector of FIGS. 3 and 4.

As discussed above, the port outlet connector 38 and the bore 40 in the housing 24 define a combination filter system, exit port and catheter attachment site. Referring to FIGS. 7 and 8, the port outlet connector 38 is a cylindrical shaft having a main body 70, a neck 72 and a head 74. The end of the main body 70 meeting neck 72 is a straight cylinder 73 and is sized to fit snugly in the cylindrical bore 40 in the housing 24. The remaining portion of the main body 70 extends from the housing 24 and has conventional barbs 76 for attaching a catheter (not shown). An axial bore 78 extends centrally through the main body 70 of the port outlet connector 38 from the barbed end to the neck 72.

The head 74 also is a straight cylinder. The neck 72 defines a tapering cylinder, with the larger end meeting the head 74. The head 74 and neck 72 have a smaller diameter than that of the cylindrical bore 40 in the housing 24 into which they fit. The walls of the cylindrical bore 40 in the housing 24 and the head and neck 72, 74 define an annular space 80 communicating with the injecting chamber 21. This annular space 80 also communicates with the axial bore 78 in the main body 70 via a transverse bore 82 through the neck 72. Thus, fluid injected into the injection chamber 21 flows through the annular space 80, into the transverse bore 82, then into the axial bore 78 and finally into the catheter (not shown). The catheter delivers the fluid to the appropriate body location.

Figure 9:
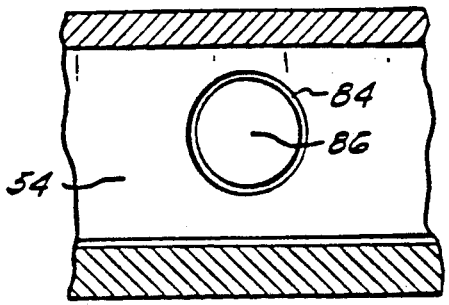
FIG. 9 is a cross-sectional view along lines 9—9 of FIG. 2.
Figure 11:
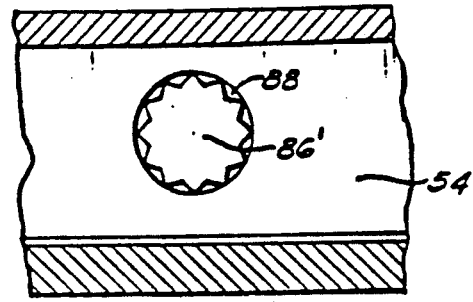
FIG. 11 is a cross-sectional view similar to FIG. 9 using the device of FIG. 10.
Figure 10:
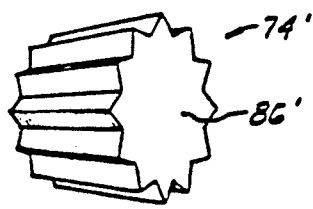
FIG. 10 is a side view of the head and neck region of another embodiment of the port outlet connector of the invention.

Referring to FIG. 9, the filter space 84 between the terminal end 86 of the head 74 and the neck base wall 54 of the injection chamber 21 defines the injection port filter. As shown in FIG. 9, the terminal end 86 of the head 74 is positioned flush with the neck base wall 54 of the injection chamber 21. The peripheral surface of the terminal end 86 of the connector head 74 may be smooth such that the filter space 84 is an open ring. Alternatively, as shown in FIG. 10 the peripheral surface of the terminal end 86' of the head 74' may be notched so that a ring of holes 88 (FIG. 11) rather than an open ring defines the filter.

Preferably the cross-sectional filter area (the area of the ring shown in FIG. 9 or the sum of the area of the individual holes shown in FIG. 11) is greater than the cross-sectional area of the exit and delivery path (the smaller of the transverse bore, the axial bore and the catheter inside diameter). Fluid restriction is removed under these conditions. If the cross-sectional filter area is less than the cross sectional area of the exit and delivery path, then preferably the walls of the head 74 and neck 72 taper quickly from the terminal end 86 of the head 74 to relieve fluid restriction.

In the embodiment described, the port outlet connector 38 is welded to the bore 40, the weld having a maximum width 0.050". The welded assembly does not leak air when tested at 45 PSI for 5 seconds.

The filter of the invention is extremely simple to manufacture as only two parts are required. It is particularly useful for the small side-entry injection port because it simplifies the difficulties involved with manufacturing, manipulating and attaching a small, separate part. In particular, it eliminates manufacturing and attaching a small filter as a separate element of the injection port. It should be understood however, that the filter may be used in any injection port regardless of size and further may be useful in devices other than injection ports.

Figure 12:
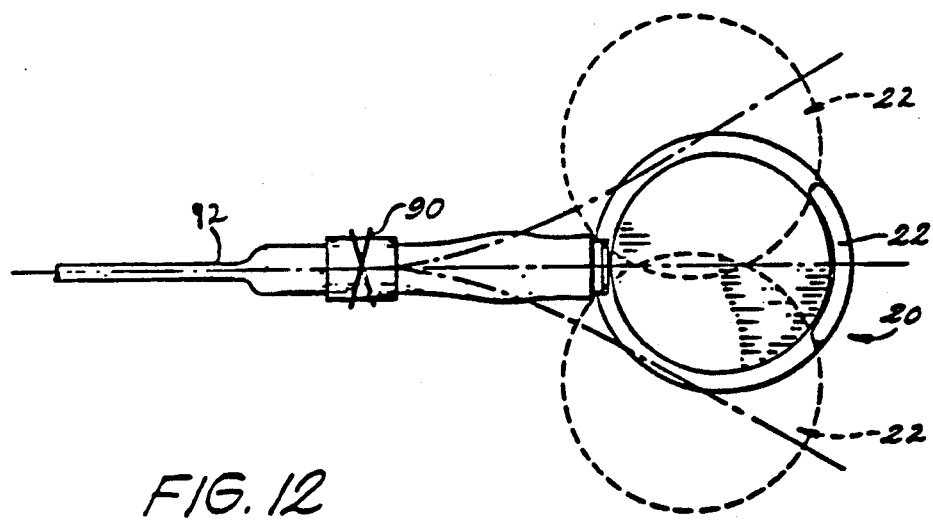
FIG. 12 shows the attachment of the injection port of the invention by a suture tab allowing limited rotation of the device when implanted.

Referring to FIG. 12, the side-entry injection port 20 may be provided with a suture-tab 90. The suture tab may be made of silicone rubber and designed as a sleeve to be fitted over a catheter 92 which is in turn slipped over the barbed region of the port outlet connector 38. The suture tab 90 may be provided with suture wings 91 which extend laterally from the port outlet connector 38 when the suture tab 90 is in place. Each of the suture wings 91 may be sutured to subcutaneous tissue to secure the injection port 20 in place beneath the skin. Alternatively, the suture tab 90 may be sutured at or about a single location, on one of the suture wings only, remote from the puncture face of the septum 22 so that the face of the septum 22 may be rotated substantially parallel to the skin about the axis defined by the point of attachment. Thus, as shown in FIG. 12, the puncture surface of the septum 22 may be directed to a broader area of the skin than if no rotation were possible. In this manner, the trauma caused by the multiple puncture of the skin at a single location is reduced. Also, the movement helps to dissipate stress caused and associated tissue trauma when pressure is applied to the skin at or near the implanted device.

To implant the device, an incision is made in the skin. Then the side entry-injection port is placed beneath the skin, attaching the injection port by the suture tab to the subcutaneous tissue. The puncture surface of the septum preferably is directed away from the incision and the puncture surface of the septum is oriented substantially perpendicular to the surface of the skin. Then the incision is closed.

Accessing the implanted device is facilitated by locating the exit port directly opposite the puncture face of the septum. To access the implanted side entry injection port, the device is grasped at the exit port between the thumb and the finger, and a needle is directed substantially parallel to the surface of the skin toward the septum by aiming at the V created by the thumb and the finger. The needle insertion pressure is discontinued when the needle abutting against the stop or solid base wall of the injection chamber is detected.

Figure 13A:
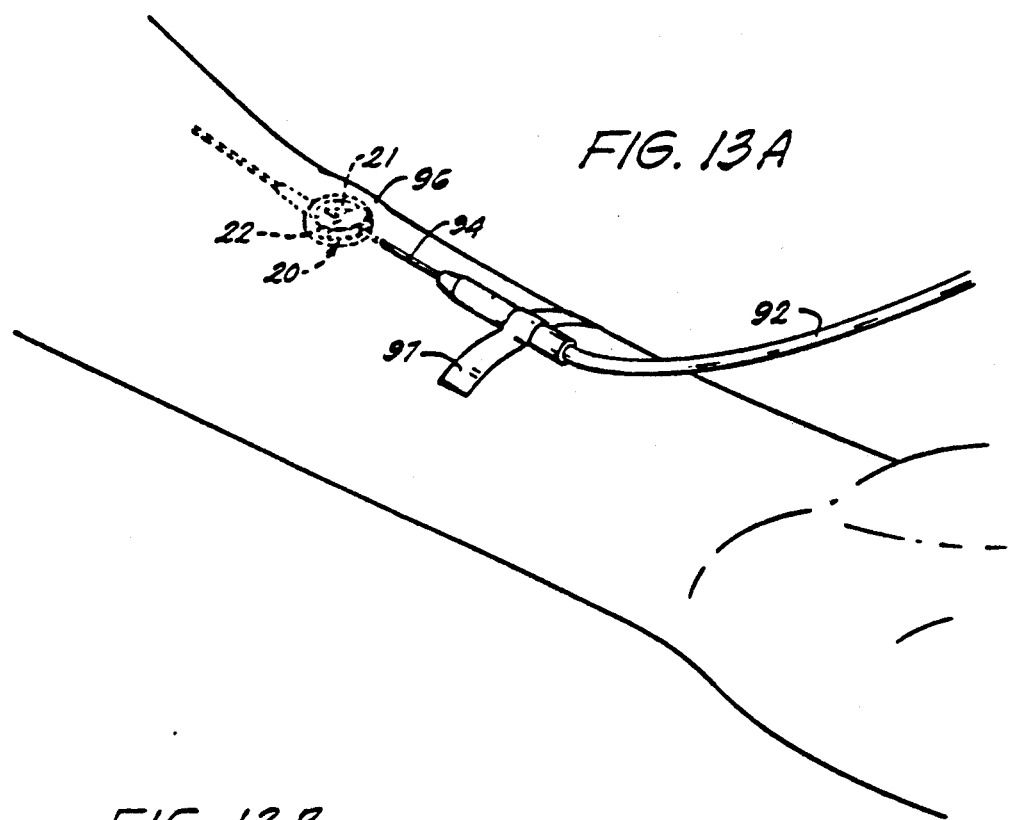
FIG. 13A is a schematic representation of the side-entry port of the invention implanted beneath the skin.
Figure 13B:
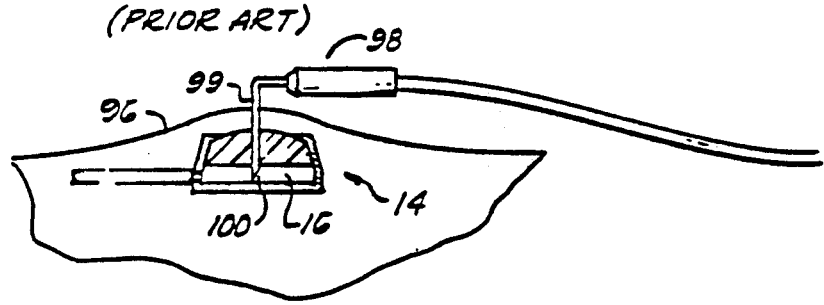
FIG. 13B is a schematic representation of the typical prior art device implanted beneath the skin.

FIG. 13A illustrates the side entry port of the invention when implanted and set up for a long-term access, as compared with a typical prior art top entry device shown in FIG. 13B. A straight needle 94 is shown accessing the side-entry injection port 20. The straight needle 94 passes substantially parallel to the surface of the skin 96, through the skin 96 and septum 22, and into the injection chamber 21. Because the needle is straight, it is inserted in a routine manner using commonly practiced venipuncture techniques. To secure the needle in place for long-term access, the needle is simply taped (shown at 97) to the skin.

In the prior art device, typically a right angle needle 98 is used for long-term access of the injection port 14. As shown, the right angle needle 98 must be inserted perpendicular to the skin 96 to access the injection chamber 16. As can be easily understood, if the distal portion 99 of the right angle needle 98 entering through the skin and septum to access the injection chamber 16 is not the proper length, the needle end 100 either will not reach the injection chamber (if the portion 99 is too short) or the right angle bend will be raised off the skin (if the portion 99 is too long). Either result is undesirable. Therefore, the right angle needle 98 must be properly sized for each patient to conform to the depth of implantation of the device and the thickness of the fatty tissue overlaying the implanted device. According to the side-entry port of the invention, a straight needle of any virtually any size may be used, and the problem of selecting the proper needle size in the prior art is obviated. Additionally, forces perpendicular to the surface of the skin have been known to cause right angle needles to back out of the injection chamber of the implanted device. Such forces perpendicular to the skin would not affect the placement of a needle accessing a side-entry injection port.

Semi-rigid catheters may be used for long term access of subcutaneous injection ports. When catheters are used with the top entry devices of the prior art, special anti-kink brackets would be required to allow the catheter which exits perpendicularly to the skin to be bent over and taped to the skin without kinking. When a side-entry injection port is used, the catheter exits the skin substantially parallel to the skin and the problem of kinking also is obviated.

Figure 14:
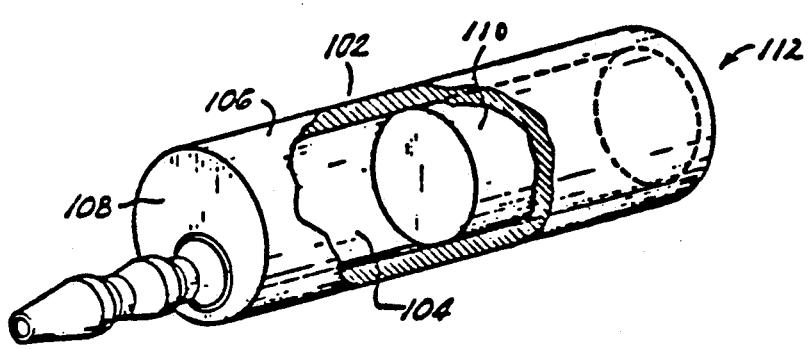
FIG. 14 shows another embodiment of the side-entry port of the invention.

It should be understood that other embodiments of a side entry injection port may be substituted for the embodiment described above. For example, as shown in FIG. 14, the rigid housing 102 defining the injection chamber 104 may be characterized by a tubular wall 106 closed off at one end by a rigid wall 108 and closed off at the opposite end by a septum 110 Such a device would be implanted with the tubular wall lying substantially parallel to the surface of the skin. The puncture surface 112 of the septum 110 would lie perpendicular to the surface of the skin. The tubular wall also may be flattened to define parallel upper and lower surfaces.

Various changes and modifications to the embodiments shown in the drawings and described above may be made within the scope of the invention. It, therefore, is intended that all matter contained in the above description and shown in the accompanying drawings shall be interpreted in an illustrative and not limiting sense.

What is claimed is:

1. An implantable subcutaneous injection port comprising,
    a housing, said housing having a substantially flat bottom wall and a side wall extending from the bottom wall,
    an injection chamber in said housing defined by chamber walls,
    an inlet opening in said side wall,
    a septum captured by said housing and sealing said opening in said side wall, said septum having a center line and a puncture area occupying a substantial portion of a projected side wall area of the housing when viewed along the central line of the septum, and
    an exit port communicating with said chamber, wherein the portion of the chamber walls located opposite the inlet opening is adapted to provide a stop for limiting advancement of a needle positioned through the septum.

2. An implantable subcutaneous injection port as claimed in claim 1, wherein the housing is metal.

3. An implantable subcutaneous injection port as claimed in claim 1, wherein the septum has an outside facing surface, and wherein the distance from the outside facing surface of the septum to the portion of the chamber walls located opposite the inlet opening is greater than the height of the injection chamber.

4. An implantable subcutaneous injection port as claimed in claim 3, wherein the distance from the outside facing surface of the septum to the portion of the chamber walls located opposite the inlet opening is greater than the height of the housing.

5. An implantable subcutaneous injection port as claimed in claim 1, wherein the height of the housing is about ⅜ of an inch.

6. An implantable subcutaneous injection port for implantation under the surface of a patient's skin, comprising,
    a housing defining an injection chamber and having a wall,
    an inlet communicating via the wall with the injection chamber,
    a septum sealing the inlet and having a center line, the septum having an outside facing surface occupying a substantial portion of a projected side wall area of the housing when viewed along the center line of the septum,
    a chamber wall located opposite the inlet and providing a stop adapted to limit advancement of a needle positioned through the septum, and
    an outlet communicating with the injection chamber, wherein the injection port is constructed and arranged such that the outside facing surface of the septum will be oriented substantially perpendicular to the surface of the patient's skin when implanted, whereby access to the injection chamber may be achieved using a straight needle introduced substantially parallel to the surface of the patient's skin.

7. An implantable subcutaneous injection port as claimed in claim 6, wherein the housing is metal.

8. An implantable subcutaneous injection port as claimed in claim 6, wherein the distance from the outside facing surface of the septum to the chamber wall opposite the septum is greater than the height of the injection chamber.

9. An implantable subcutaneous injection port as claimed in claim 8, wherein the distance from the outside facing surface of the septum to the chamber wall located opposite the septum is greater than the height of the housing.

10. An implantable subcutaneous injection port as claimed in claim 6, wherein the height of the housing is about ⅜ of an inch.

* * * * *